(12) United States Patent
Akiba

(10) Patent No.: US 7,568,735 B2
(45) Date of Patent: Aug. 4, 2009

(54) FLUID DELIVERY ADAPTER UNIT FOR ENDOSCOPE

(75) Inventor: Haruo Akiba, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 23 days.

(21) Appl. No.: 11/635,089

(22) Filed: Dec. 7, 2006

(65) Prior Publication Data

US 2007/0145738 A1 Jun. 28, 2007

Related U.S. Application Data

(63) Continuation of application No. 10/869,950, filed on Jun. 18, 2004, now abandoned.

(30) Foreign Application Priority Data

Jun. 20, 2003 (JP) ............................. 2003-175799

(51) Int. Cl.
*F16L 43/00* (2006.01)
(52) U.S. Cl. ...................................... 285/179; 285/317
(58) Field of Classification Search ................. 285/179, 285/282, 307, 317, 144.1, 181
See application file for complete search history.

(56) References Cited

U.S. PATENT DOCUMENTS 4,205,683 A 6/1980 O'Neill
5,586,791 A 12/1996 Kirchner et al.

FOREIGN PATENT DOCUMENTS

JP 2001-292963 10/2001

*Primary Examiner*—Aaron M Dunwoody
(74) *Attorney, Agent, or Firm*—Young & Thompson

(57) ABSTRACT

A fluid delivery adapter unit for selectively connecting fluid supply equipments to an endoscope that includes a straight pipe capable of being detachably coupled to a fluid inlet collet of a headpiece of the endoscope and a generally L-shaped elbow pipe having a LUER-LOK® lock component at a proximal end to which the fluid supply equipment is coupled. A joining structure is installed between the elbow pipe and the straight pipe so as to allow the elbow pipe and the straight pipe to turn through a predetermined angle relative to each other only when the elbow pipe is forced to turn and further to keep them in a turned position while the elbow pipe is unforced. The joining structure includes an elastic sealing member to provide fluid tight seal between the elbow pipe and the straight pipe.

6 Claims, 5 Drawing Sheets

FLUID DELIVERY ADAPTER UNIT FOR ENDOSCOPE

BACKGROUND OF THE INVENTION

1. Field of the Invention

The present invention relates to a fluid delivery adapter unit for an endoscope that is used as an auxiliary fluid delivery unit for selectively interfacing fluid supply equipments with an endoscope to deliver and spray fluid through a distal end of a flexible insertion tube of the endoscope.

2. Description of Related Art

Typically, an endoscope is provided with a plurality of fluid delivery and suction means for delivering and sucking fluid. One of such fluid delivery and suction means is a body-fluid suction device including a suction tube that is detachably connected to a working channel of the endoscope through which a medical instrument such as a biopsy sampling device, catheter, etc. and a vacuum pump connected to the suction tube. Suction of a body fluid is performed by operating a suction valve installed to an operating headpiece of the endoscope. In the event where it is required to clean a viewing window at a distal end of an insertion tube of the endoscope, a cleaning fluid delivery means is used to deliver a cleaning liquid to the distal end of the insertion tube. The cleaning fluid generally consists of a cleaning liquid such as water and pressurized air. Cleaning of a disfeature viewing window is performed by spraying a cleaning liquid onto the viewing window to wash away crud and/or grime and then delivering pressurized air to blow off drops of liquid from the viewing window.

As just described, endoscopes are typically provided with a liquid delivery passage and an air delivery passage. Delivery of liquid and air are selectively started by manipulation of a liquid/air delivery valve installed to the operating headpiece. In many instances, these liquid delivery passage and air delivery passage are merged together into one outlet port at their distal ends so that the outlet port is connected to a spray nozzle oriented toward the viewing window at a distal end of the insertion tube. In such an instance, cleaning of the viewing window is performed by operating the liquid/air delivery valve to cause deliver and spray of a cleaning liquid through the spray nozzle in the first place and then switching the liquid/air delivery valve to cause deliver and spray of pressurized air through the spray nozzle in the second place. In this manner, cleaning of the disfeatured viewing window of the endoscope is performed while the insertion tube remains left within a body cavity of a patient.

A certain type of endoscope is provided with fluid delivery means for spraying high pressure water against a wall surface of a body cavity of a patient so as thereby to remove away crud adhered to the wall surface of the body cavity or to disperse a dye solution toward the wall surface of the body cavity. This type of fluid delivery means causes a jet stream of desired liquid through an injection nozzle at a distal end of the insertion tube of the endocope. In this instance, it is different from the fluid delivery means for cleaning a viewing window that sprays a cleaning liquid toward the viewing window in that the liquid is sprayed in a direction of the field of view through the injection nozzle.

The fluid delivery means has a fluid outlet port at a distal end of the insertion tube and a fluid inlet port that is located on the operating headpiece. A large variety of locations of the fluid inlet port are possible. In the case where the fluid inlet port is located at an end of the operating headpiece opposite to an end from which the insertion tube extends, the fluid delivery passage extends approximately straight between the fluid inlet port to the fluid outlet port. This is advantageous from the viewpoint of cleaning the interior of the fluid delivery passage. In order to supply a high pressure fluid, a fluid supply equipment is connected to the endoscope through the fluid inlet port-that generally comprises a fluid tank, a fluid conveyance tube and a fluid supply pump.

In the meanwhile, endoscopes are provided with a universal tube or sheath extending from an operating headpiece which encloses light guide means for guiding light for illuminating a body cavity from a light source provided separately from the endoscope and, in the case of electronic endoscope, a video signal transmission cable for transmitting video signals from a CCD image pick-up device at a distal end of an insertion tube of the endoscope to a vide monitor provided separately from the endoscope. In the case where an endoscope is connected with the fluid conveyance tube in addition to the universal tube at the operating headpiece, the fluid conveyance tube possibly gets in operator's hair when the operator manipulates the endoscope taking a grip on the operating headpiece. Furthermore, there is fear that the fluid conveyance tube is broken near the fluid inlet port and, in that event, blocks desirable delivery of fluid. For these reason, it may be desirable to use a generally L-shaped plumbing connector pipe to connect a fluid conveyance tube to the fluid inlet port so that fluid conveyance tube extends in the approximately same direction as the universal tube, as described more fully, for example, in Japanese Unexamined Patent Publication No. 2001-292963.

Fluid supply equipments for use with the endoscope include manual type fluid supply equipments such as a syringe that is manipulated by a surgical practitioner apart from the pumping type fluid supply equipment. Manual fluid supply using a syringe capacitates a surgical practitioner to perform unrestrained quantity and/or pressure control of fluid delivery and is often preferred depending on the end of fuel delivery. However, the prior art fuel delivery system has a problem with connectivity of the plumbing connector pipe with a syringe or operationality of a syringe connected to the plumbing connector pipe resulting from directional consistency between the plumbing connector pipe and the universal tube. In particular, since the plumbing connector pipe faces downward when taking a single-handed grip on the operating headpiece of the endoscope, manipulation of the syringe with the other hand is inevitably accompanied by awkward motion with the consequence that it is hard for the surgical practitioner to impart injection force to the syringe.

SUMMARY OF THE INVENTION

It is therefore an object of the present invention to provide a fluid delivery adapter unit for selectively connecting fluid supply equipments to an endoscope that enables a surgical practitioner taking a single-handed grip on an operating headpiece of the endoscope to manipulate the endoscope with the other hand without being encumbered by a fluid conveyance tube of a pumping type fluid supply equipment or to perform smooth manipulate of a manual type fluid supply equipment such as a syringe or the like.

The foregoing object of the present invention is accomplished by a fluid delivery adapter unit for selectively connecting fluid supply equipments to an endoscope comprising an operating headpiece, an elongated insertion tube extending from the operating headpiece, and fluid delivery passage means that extends from fluid inlet means such as a collet opening at a proximal end of the operating headpiece and coupling a fluid supply equipment to the endoscope to fluid outlet means at a distal end of the elongated insertion tube so as to deliver fluid supplied from the fluid supply equipment to the fluid outlet means. The fluid delivery adapter unit comprises a straight pipe capable of being detachably coupled to the fluid inlet means, an elbow pipe having a LUER-LOK® lock component at a proximal end to which the fluid supply equipment is coupled, and joining means for joining the elbow pipe to the straight pipe so as to allow the elbow pipe to turn in opposite directions, desirably through a predetermined angle in a range from 90 to 180°, relatively to the straight pipe only when the elbow pipe is forced to turn and to keep the elbow pipe in a turned position with respect to the straight pipe while the elbow pipe is unforced.

It is preferred that the elbow pipe is bent at an angle of approximately 90° so as to have a generally L-shaped configuration for the purpose of structural simplicity. It is preferred that the elbow pipe is partly inserted into the straight pipe. In this instance, the joining means comprises elastic sealing means disposed on portion of the elbow pipe inserted in the straight pipe and compressed between the elbow pipe and the straight pipe so as to provide fluid tight seal between them while allowing the elbow pipe to turn with respect to the straight pipe against frictional force of the elastic sealing means. The joining means comprising the elastic sealing means between the elbow pipe and the straight pipe keeps the elbow pipe in a turned position with its frictional force. In consequence the joining means thus structured is more advantageous to position adjustment of the elbow pipe than comprising a mechanical locking member or mechanical locking device.

BRIEF DESCRIPTION OF THE DRAWINGS

The above and other objects and features of the present invention will be clearly understood from the following detailed description when read with reference to the accompanying drawings, wherein the same numeral numbers have been used to denote same or similar parts or mechanisms throughout the drawings and in which.

DETAILED DESCRIPTION OF THE PREFERRED EMBODIMENT

In the following description, the term "distal end" as used herein shall mean and refer to the end close to a distal end of an insertion tube of an endoscope, and the term "proximal end" as used herein shall mean and refer to the end remote from the a distal end of an insertion tube of an endoscope.

Figure 1:
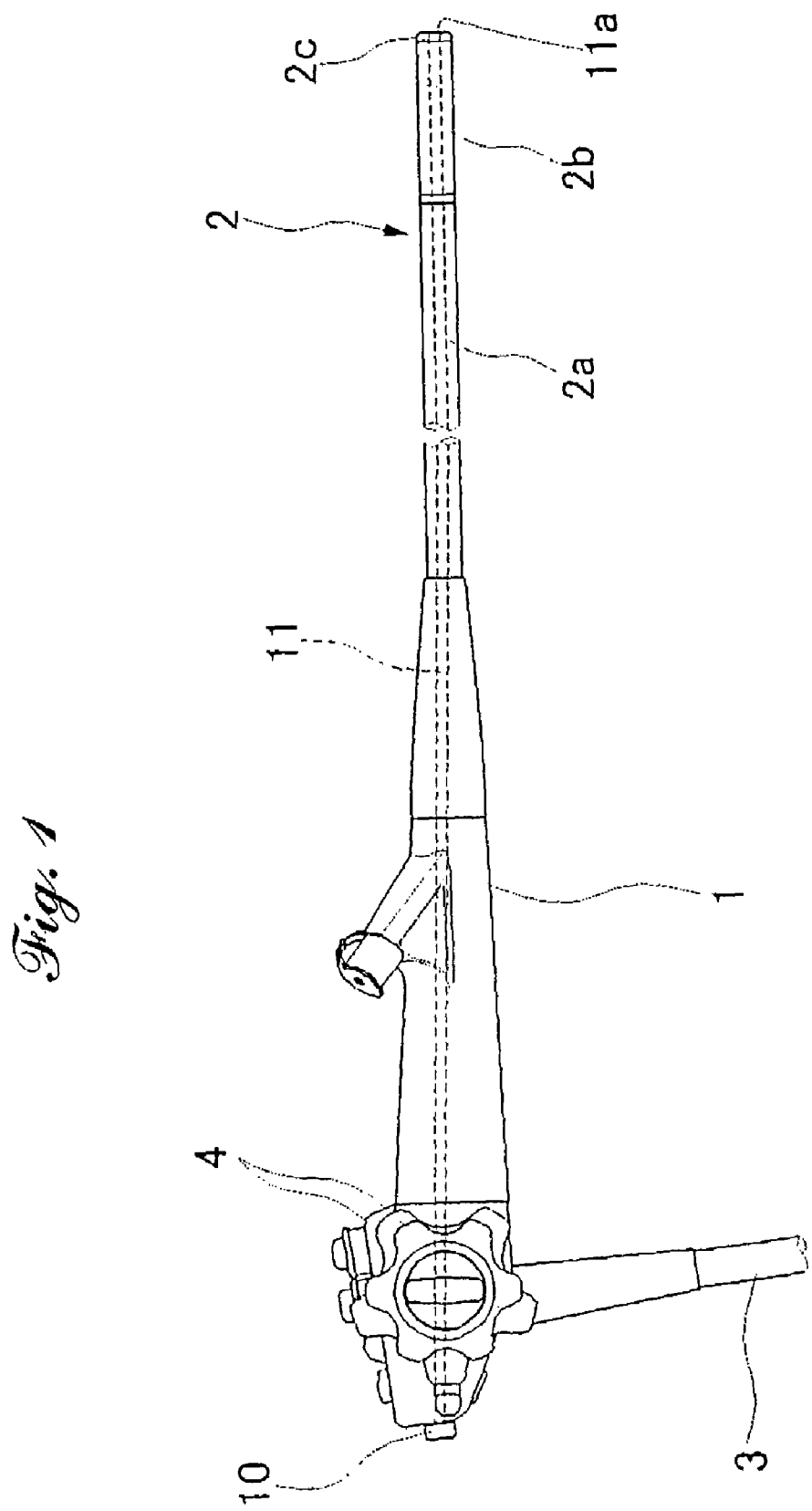
FIG. 1 is an external view of an endoscope equipped with a fluid deliver, adapter unit according to an embodiment of the present invention.

Referring to the drawings in detail, and, in particular, to FIG. 1 schematically showing an endoscope, the endoscope comprises an operating headpiece 1, an elongated insertion tube 2 connected to the operating headpiece 1, and a universal tube 3 connected to the operating headpiece 1. The insertion tube 2 that is inserted into a body cavity of a patient (not shown) consists of a soft tube portion 2a, a flexible tube portion 2b and a rigid distal tube portion 2c in order from the side of the operating headpiece 1 to the distal end. The distal tube portion 2c is provided with an endoscopic observation system comprising an observation unit and an illumination unit installed therein. The flexible tube section 2b can be bent in any direction by a pair of articulation control knobs 4 installed to the operating headpiece 1 so as thereby to orient the distal tube portion 2c in desired directions.

The endoscope is equipped with fluid delivery means, called a fluid-jet spray device or an auxiliary water delivery device, installed therein through which fluid such as water or a chemical solution is delivered and sprayed toward a wall surface of a body cavity of a patient. The fluid delivery device has fluid inlet means 10 such as a collet secured to the operating headpiece 1 and a fluid delivery channel 11 extending inside the insertion tube 2 from the fluid inlet collet 10 and having fluid spray means such as a spray nozzle 11a opening to the endoscopic observation system at an extremity of the distal tube portion 2c. The fluid inlet collet 10 is installed in the operating headpiece 1 at an end in a lengthwise direction of the endoscope opposite to an end at which the insertion tube 2 is connected to the operating headpiece 1. This location of the fluid inlet port 10 makes the fluid delivery channel 11 lay approximately straight within the operating headpiece 1 with the consequence that the fluid delivery channel 11 near the fluid inlet collet 10 can be cleaned with a brush.

Figure 2:
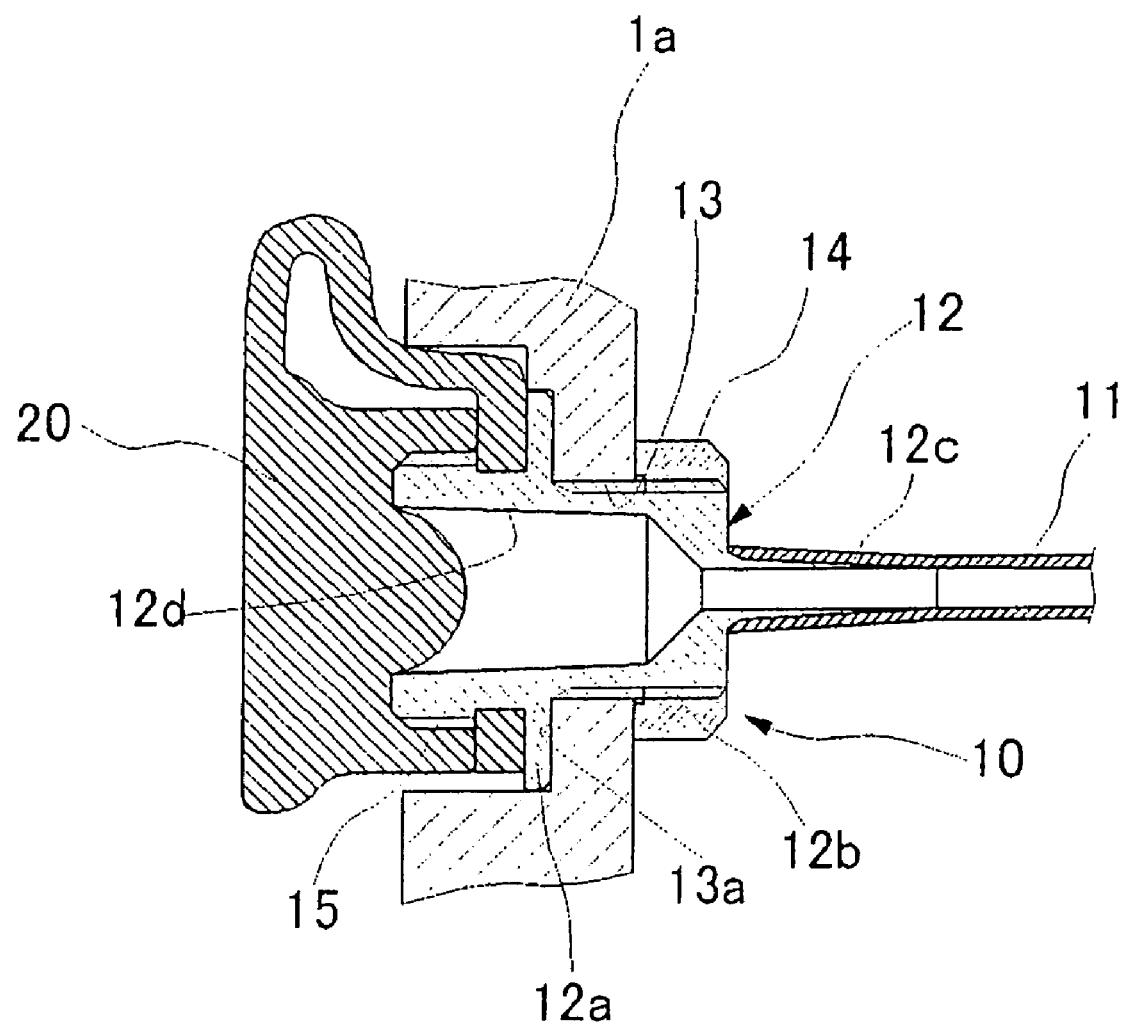
FIG. 2 is a sectional-view of a fluid inlet port with a plug put thereon.
Figure 3:
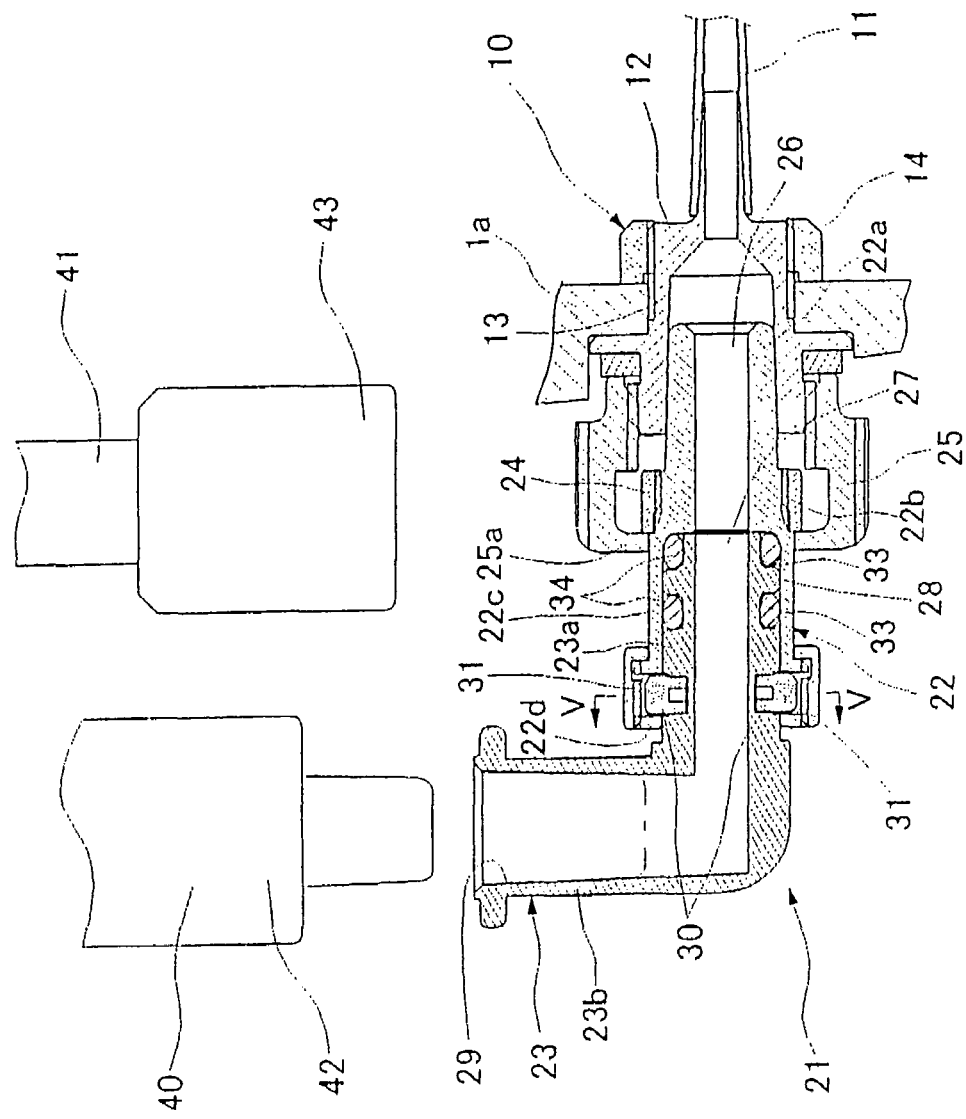
FIG. 3 is a sectional-view of the fluid delivery adapter unit connected to a fluid inlet port.

As shown in FIGS. 2 and 3, the fluid inlet collet 10 includes a flanged inlet coupler 12 having a generally cylindrical shape and fitted into a stepped mounting bore 13 formed in a housing 1a of the operating headpiece 1. The inlet coupler 12 has an annular flange 12a that is snugly situated on a stepped seat 13a of the mounting bore 13 when the inlet coupler 12 is mounted in the mounting bore 13 and has external threads 12b formed on external surface thereof behind the flange 12a, i.e. portion of the inlet coupler 12 that is located within and hidden by the housing 1a of the operating headpiece 1. The inlet coupler 12 is firmly secured to the housing 1a of the operating headpiece 1 by fastening a setscrew 14 onto the external threads 12a of the inlet coupler 12 so as to tightly hold portion of the housing 1a between the flange 12a and the setscrew 14. The inlet coupler 12 further has a tapered coupling sleeve 12c formed as an integral piece of the inlet coupler 12. The inlet coupler 12 is coupled onto a tube forming the fluid delivery channel 11 through the coupling sleeve 12c.

The inlet coupler 12 formed as a female LUER-LOK® lock component has a conical bore 12d opening at the proximal end thereof The conical bore 12d is formed such that the bore diameter linearly decreases along a predetermined lengthwise distance from the proximal end thereof and an inclination of the conical surface is approximately 6/100 that is comparatively gentle. The inlet coupler 12 has external threads 15 extending on an external surface thereof from the proximal end to a position at a predetermined lengthwise direction from the flange 12a.

When the inlet coupler 12 is left open during insertion of the insertion tube 2 into a body cavity of a patient, the body cavity is brought into communication with the atmosphere through the fluid delivery channel 11 extending between the inlet coupler 12 and the spray nozzle 11a. In order to interrupt the communication between a body cavity and the atmosphere, a plug 20 is detachably fitted into the conical bore 12d of the inlet coupler 12. In the event where a delivery of fluid into a body cavity is required, a fluid supply equipment, that is provided separately from the endoscope, is connected to the endscope through a fluid delivery adapter 21 detachably connected to the inlet coupler 12 in place of the plug 20 as shown in FIG. 3.

Figure 4:
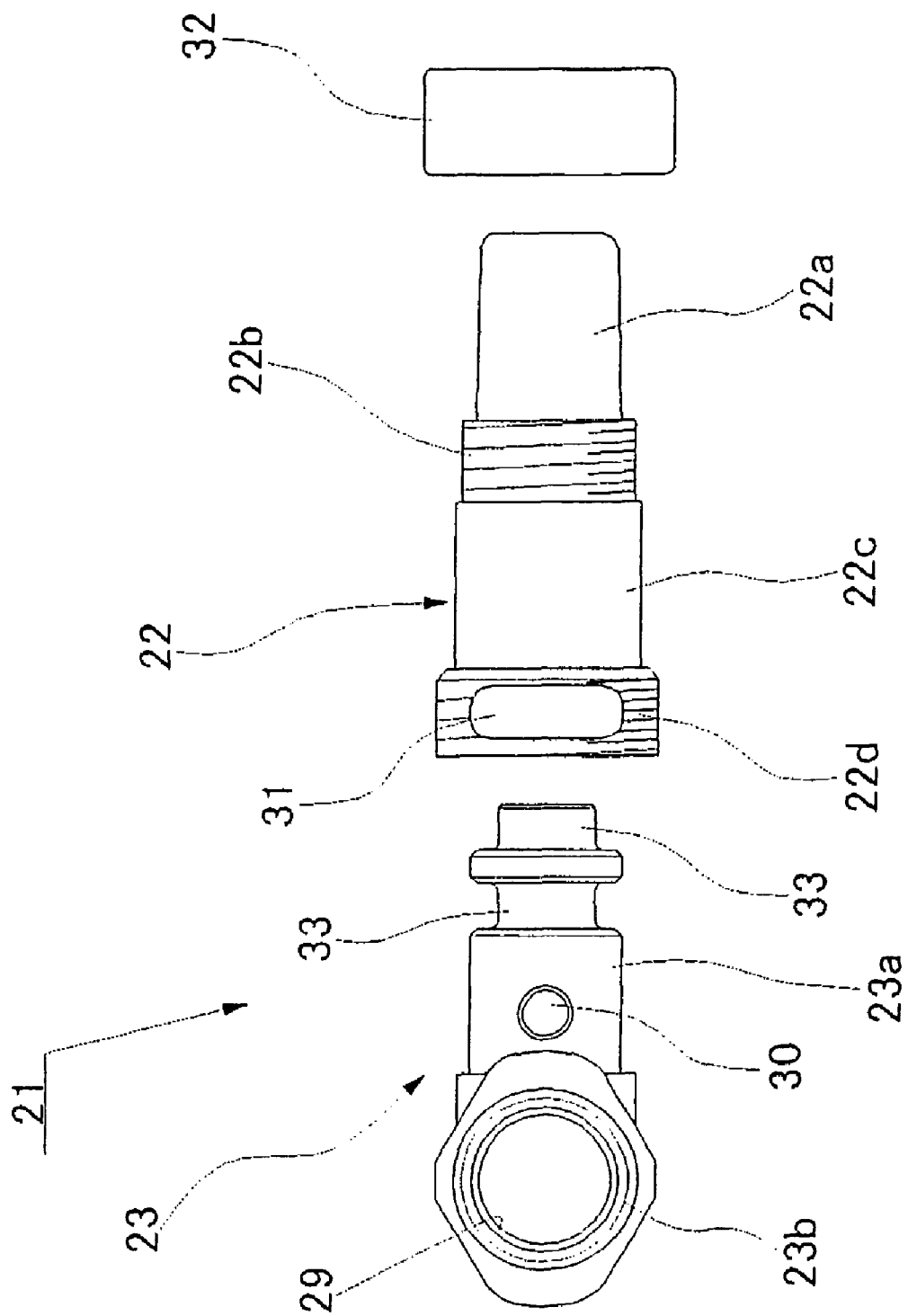
FIG. 4 is a plan view of the fluid delivery adapter unit exploded by component.

As shown in detail in FIGS. 3 and 4, the fluid delivery adapter 21 comprises two pipes, namely a straight coupling pipe 22 that is detachably connected to the inlet coupler 12 and an elbow pipe 23 loosely joined to the coupling pipe 22. The coupling pipe 22 is made as an integral piece having a fluid flow passageway 26. The coupling pipe 22 consists of four pipe portions, namely a coupling pipe portion 22a, a threaded pipe portion 22b, an enlarged pipe portion 22c and a thick collar portion 22d arranged in this order. The coupling pipe portion 22a is tapered off or cone-shaped as a male LUER-LOK® lock component so as to snugly mate with the conical bore 12d of the inlet coupler 12. The threaded pipe portion 22b has external threads formed on an outer surface thereof so as to have a thread diameter greater than that of the coupling pipe portion 22a. The enlarged pipe portion 22c has an external diameter greater than the thread diameter of the threaded pipe portion 22b but less than an external diameter of the cylindrical portion of the inlet coupler 12 and has a socket bore 28 for receiving the elbow pipe 23 for conjunction. The thick collar 22d has a pair of elliptic holes 31 in its perimeter wall at diametrically opposite positions. A threaded union ring 24 having an external diameter less than the external diameter of the cylindrical portion of the inlet coupler 12 but greater than an external diameter of the enlarged pipe portion 22c of the coupling pipe 22. A union nut 25 is loosely fitted onto the enlarged pipe portion 22c of the coupling pipe 22 and is configured to fasten onto the external threads 15 of the inlet coupler 12. The union nut 25 has an annular collar 25a having an inner diameter greater than the external diameter of the union ring 24 but smaller than the external diameter of the enlarged pipe portion 22c of the coupling pipe 22. In the way of fastening the union nut 25 onto the inlet coupler 12, the union nut 25 forces the annular collar 25a to push down the union ring 24 and, in consequence, to drive the coupling pipe portion 22a of the coupling pipe 22 into the conical bore 12d of the inlet coupler 12. When the union nut 25 is fully fastened onto the inlet coupler 12, the coupling pipe 22 is locked up in the inlet coupler 12. On the other hand, when the union nut 25 is unfastened from the inlet coupler 12, the coupling pipe 22 is uncoupled from the inlet coupler 12.

The elbow pipe 23 is made as an integral piece having a fluid flow passageway 27 in straight fluid communication with the fluid flow passageway 26 of the coupling pipe 22 and a fluid flow passageway 29 extending at approximately 90° from the fluid flow passageway 27. Specifically, the elbow pipe 23 consists of two pipe portions, namely a relay pipe portion 23a that is connected to the coupling pipe 22 and a coupling pipe portion 23b extending at approximately 90° from the relay pipe portion 22a. The fluid flow passageway 27 is formed in the relay pipe portion 23a so as to be in fluid communication with the fluid flow passageway 27. The fluid flow passageway 29 is formed in the coupling pipe portion 23b so as to form a female LUER-LOK® lock component. That is, the fluid flow passageway 29 is tapered such that the inner diameter of the passageway 29 linearly decreases along a predetermined lengthwise distance from an open end thereof (as shown by the phantom line in FIG. 3). The elbow pipe 23 is coupled onto and locked up in an auxiliary equipment having a coupling distal end forming a male LUER-LOK® lock component by mating the coupling distal end into the tapered fluid flow passageway 29 of the coupling pipe portion 23b of the elbow pipe 23. For coupling convenience of the elbow pipe 23 onto the auxiliary equipment, the elbow pipe 23 is provided with an annular flange as shown in FIG. 3.

The elbow pipe 23 may be equipped with a plug (not shown) that is detachably fitted into the fluid flow passageway 29 of the coupling pipe portion 23b while the auxiliary equipment remains uncoupled.

As was previously described, the elbow pipe 23 is inseparably joined to the coupling pipe 22 through slightly slack insertion of the relay pipe portion 23a in the socket bore 28 of the coupling pipe 22. In order to provide tight conjunction between the elbow pipe 23 and the coupling pipe 22 for properly coupling the endoscope and the fluid supply equipment together in desired relative positions, the elbow pipe 23 is allowed to turn in the socket bore 28 of the coupling pipe 22 through a predetermined angle in opposite directions and is fixedly joined to the coupling pipe 22 in a desired relative position.

Figure 5:
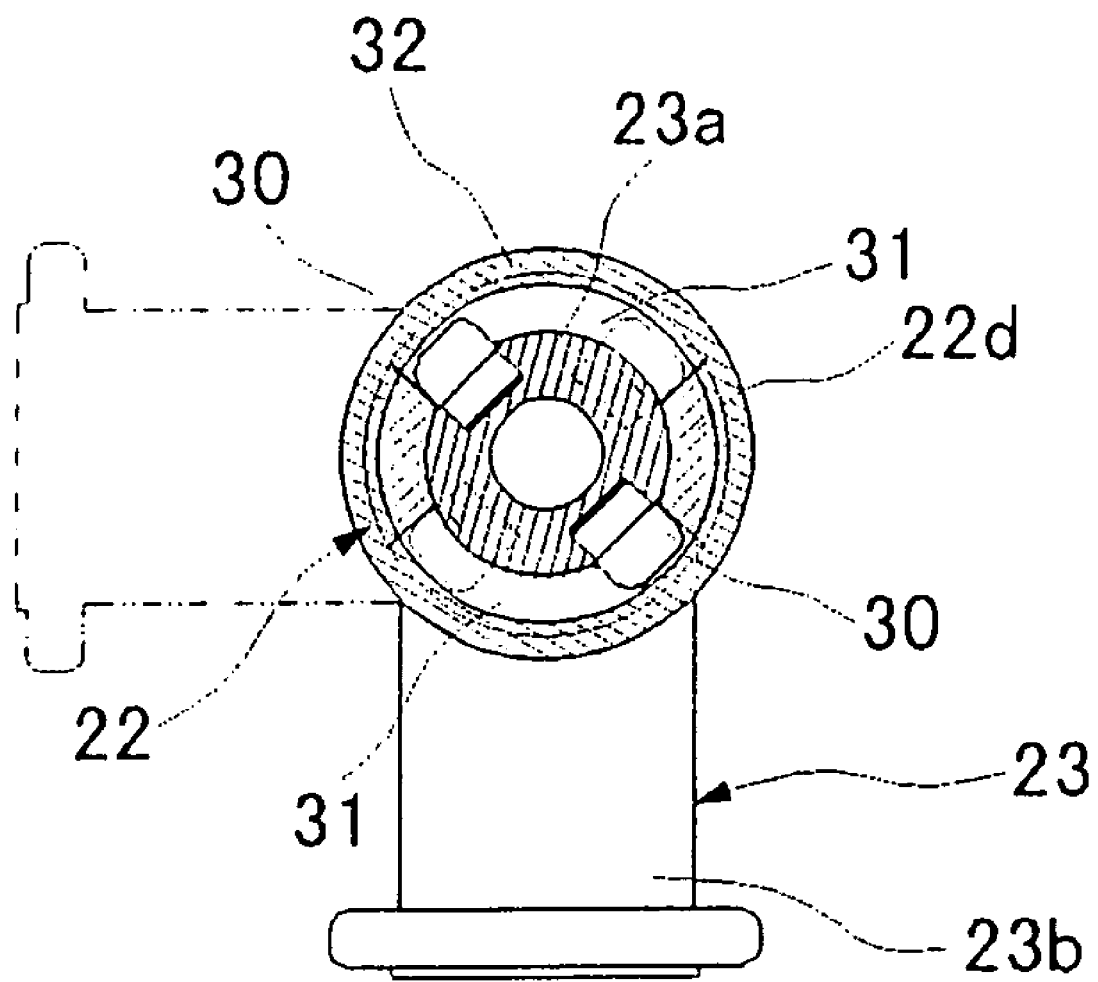
FIG. 5 is a cross-sectional view of FIG. 3 taken along line V-V.

Referring to FIG. 5 showing a position adjusting mechanism for adjusting the elbow pipe 23 in position or direction relative to the coupling pipe 22, the elbow pipe 23 is provided with a pair of cylindrical latch hooks 30 having, an external diameter approximately equal to a width of the elliptic hole 31 of the thick collar 22d of the coupling pipe 22. These latch hooks 30 are fixedly disposed in diametrically opposite positions on the relay pipe portion 23a and are press-fitted in, or otherwise fixedly attached to, the relay pipe portion 23a so as to be movably received in the elliptic hole 31 of the thick collar 22d. The latch hooks 30 are in the elliptic holes 31 of the thick collar 22d. respectively, Accordingly, the elbow pipe 23 can turn relatively to the coupling pipe 22 so as thereby to be adjusted in position or direction relative to the coupling pipe 22. The circumferentially movable engagement between the latch hooks 30 and the elliptic holes 31 prevents the elbow pipe 23 from axially displacing, and hence being separated, from the coupling pipe 22. In this instance, it is desired for the elliptic hole 31 to have an aperture angle in a range of from approximately 90° to approximately 180° so that the elbow pipe 23 can turn through a predetermined angle, for example, up to 90° relatively to the coupling pipe 22 in this embodiment, as shown by the phantom lines in FIG. 5. Further, it is preferred to cover the thick collar 22d with an ornamental ring cap 32.

As shown in FIGS. 3 and 4 in detail, the elbow pipe 23 is rotatably joined to the coupling pipe 22 through joining means principally involving elastic sealing means. Specifically, the elbow pipe 23 is provided with two elastic sealing rings 34 such as O-rings seated on seats 33 formed on the relay pipe portion 23a. The sealing rings 34 are compressed between the seats 33 formed on the relay pipe portion 23a and the interior wall of the socket bore 28 of the enlarged pipe portion 22c of the coupling pipe 22, so as thereby to provide fluid tight seal between the coupling pipe 22 and the elbow pipe 23, in particular between the fluid flow passageways 26 and 27 formed therein. Compression strain of the sealing rings 34 keeps the elbow pipe 23 and the coupling pipe 22 in any adjusted relative position or direction. Accordingly, it is necessary for position adjustment of the elbow pipe 23, in other words, a direction adjustment of the coupling pipe portion 23b, to drive the elbow pipe 23 against frictional force of the sealing rings 34.

The fluid delivery adapter unit coupled onto the fluid inlet collet 10 of the endoscope enables a fluid supply equipment to supply fluid into a body cavity of a patient through the endoscope. When fluid delivery is not called for, the fluid delivery adapter unit is uncoupled from the endoscope and then the plug 20 is fitted into the conical bore 12d of the inlet coupler 12 of the fluid inlet collet 10 so as thereby to keep the fluid delivery channel 11 of the endoscope from remaining open to the atmosphere.

Examples of fluids to be delivered into body cavities of patients through endoscopes include a cleaning liquid for cleaning a wall surface of the body cavity, a fluid of contrast media and other chemical solutions for medical treatment. These fluids may be delivered automatically or manually. The manual fluid delivery is typically performed by use of a syringe as the fluid supply equipment. On the other hand, the automatic fluid delivery is typically performed by the aid of a fluid conveyance tube connected to a water pump. That is, the water pump draws from a fluid tank and feeds pressurized fluid into the fluid conveyance tube.

In this instance, the fluid supply equipment, a syringe or a fluid conveyance tube, may be connected to the fluid inlet collet 10 of the endoscope directly or by way of the fluid delivery adapter 21. Since the fluid delivery adapter 21 has a generally L-shaped configuration and is capable of turning through a predetermined angle, for example, of approximately 90° relative to the fluid inlet collet 10 as described above, the fluid supply equipment can be connected in all directions, i.e. from above, below or sideways. A syringe 40 and a fluid conveyance tube 41 are schematically shown by way of example of the fluid supply equipment in FIG. 3. The syringe 40 has a distal end coupler 42 formed as a male LUER-LOK® lock component mating with the female LUER-LOK® lock component at the coupling pipe portion 23b of the elbow pipe 23.

The fluid conveyance tube 41 has a distal end coupler 43 formed as a male LUER-LOK® lock component mating with the female LUER-LOK® lock component at the coupling pipe portion 23b of the elbow pipe 23. These syringe 40 and fluid conveyance tube 41 are selectively connected to the endoscope by coupling the distal end coupler 42 or 43 to the fluid delivery adapter 21. The fluid conveyance tube 41 at one end is connected to a water pump (not shown) that draws and pressurizes fluid in a fluid tank. Typically, the fluid tank is located near a light source unit (not shown) that is connected to the endoscope through the universal tube 3 (see FIG. 1). Therefore, the elbow pipe 23 of the fluid delivery adapter 21 is turned to adjust a position in the same direction as the universal tube 3. It is preferred to tie the fluid conveyance tube 41 with the universal tube 3 at more than one position with binding bands or binding tapes so that the fluid conveyance tube 41 does not lie in the way of a surgical practitioner who takes a singlehanded grip on the operating headpiece 1 of the endoscope.

On the other hand, it is quite usual for the syringe 40 to be manipulated by a surgical practitioner. That is, the surgical practitioner manipulates the syringe 40 with one hand while holding the operating headpiece 1 of the endoscope with the other hand. Therefore, it facilitates manipulation of the syringe 40 if the syringe 40 is directed laterally with respect to the operating headpiece 1 of the endoscope. In particular, it is preferred that the syringe 40 extends from the endoscope on opposite side of the operating headpiece 1 in a lengthwise direction, i.e. toward the side on which the articulation control knobs 4 are installed. By reason of this, it is preferred to connect the syringe 40 to the fluid delivery adapter 21 with the elbow pipe 23 turned 90° with respect to the relay pipe portion 22a as shown by the phantom lines in FIG. 5. This syringe position allows the surgical practitioner to handily manipulate the syringe 40 with one hand while holding the endoscope with the other hand. That is, a piston of the syringe 40 can be forced with one hand toward the other hand holding the operating headpiece 1 to douche fluid into a body cavity of a patient through the endoscope. This notably enhances operationality of the syringe. The installation of the sealing rings 34 between the coupling pipe 22 and the elbow pipe 23 which are connected for relative rotation reliably secures an adjusted angular position of the elbow pipe 23 relative to the coupling pipe 22 and prevents the elbow pipe 23 from changing its angular position during manipulation of the syringe 40. This is quite advantageous to easy and reliable manipulation of the syringe.

As described above, the fluid delivery adapter of the present invention enables a surgical practitioner taking a single-handed grip on an operating headpiece of the endoscope to manipulate the endoscope with the other hand without being encumbered by a fluid conveyance tube of a pumping type fluid supply equipment or to perform smooth manipulate of a manual type fluid supply equipment such as a syringe or the like.

The present invention has been described with reference to preferred embodiments thereof. However, it will be appreciated that variants and other embodiments can be effected by person of ordinary skill in the art without departing from the scope of the invention.

What is claimed is:

1. A fluid delivery adapter unit for selectively connecting fluid supply equipments to an endoscope comprising an operating headpiece, an elongated insertion tube extending from the operating headpiece, and fluid delivery passage means which extends from fluid inlet means which opens to the atmosphere at a proximal end of the operating headpiece and to fluid outlet means at a distal end of the elongated insertion tube and to which a fluid supply equipment is connected through the fluid inlet means so as to deliver fluid supplied from the fluid supply equipment to the fluid outlet means, said fluid delivery adapter unit comprising:

a straight pipe having a first end being detachably coupled to said fluid inlet means;

an elbow pipe having a lock component at a proximal end to which said fluid supply equipment is matingly coupled; and joining means for joining said elbow pipe to an opposing second end of said straight pipe so as to allow said elbow pipe to turn with respect to said straight pipe only when said elbow pipe is forced to turn and to keep said elbow pipe in a turned position with respect to said straight pipe while said elbow pipe is unforced and restricting the turning of the elbow pipe with respect to the straight pipe to a predetermined angular range, such that the elbow pipe can be adjusted to a rest position having any angular position with respect to the straight pipe within the predetermined range, wherein said elbow pipe comprises elastic sealing means disposed on a portion of said elbow pipe inserted in said straight pipe and compressed between said elbow pipe and said straight pipe so as to provide fluid tight seal between said straight pipe and said elbow pipe while said joining means allows said elbow pipe to turn with respect to said straight pipe against frictional force of said elastic sealing means.

2. A fluid delivery adapter unit as defined in claim 1, wherein said joining means prevents said elbow pipe from moving in an axial direction.

3. A fluid delivery adapter unit as defined in claim 1, wherein said elbow pipe is bent at an angle of approximately 90°.

4. A fluid delivery adapter unit for selectively connecting fluid supply equipments to an endoscope comprising an operating headpiece, an elongated insertion tube extending from the operating headpiece, and fluid delivery passage means which extends from fluid inlet means which opens to the atmosphere at a proximal end of the operating headpiece and to fluid outlet means at a distal end of the elongated insertion tube and to which a fluid supply equipment is connected through the fluid inlet means so as to deliver fluid supplied from the fluid supply equipment to the fluid outlet means, said fluid delivery adapter unit comprising:

a straight pipe capable of being detachably coupled to said fluid inlet means;

an elbow pipe having a lock component at a proximal end to which said fluid supply equipment is matingly coupled; and joining means for joining said elbow pipe to said straight pipe so as to allow said elbow pipe to turn with respect to said straight pipe only when said elbow pipe is forced to turn and to keep said elbow pipe in a turned position with respect to said straight pipe while said elbow pipe is unforced, the joining means restricting the turning of the elbow pipe with respect to the straight pipe to a predetermined angular range, such that the elbow pipe can be adjusted to a rest position having any angular position with respect to the straight pipe within the predetermined range, wherein the joining means comprises a pair of elliptical holes in the straight pipe and a corresponding pair of cylindrical latch hooks extending outward from an exterior of the elbow pipe so that, when assembled, the cylindrical latch hooks pass through respective ones of the elliptical holes.

5. The fluid delivery adapter unit of claim 4, wherein the predetermined angular range of respective displacement between the straight pipe and the elbow pipe is defined by a range of motion of the cylindrical latch hooks within the elliptical holes.

6. A fluid delivery adapter unit for selectively connecting fluid supply equipment to an endoscope, the endoscope comprising an operating headpiece, an elongated insertion tube extending from the operating headpiece, and fluid delivery passage which extends from a fluid inlet, which opens to atmosphere at a proximal end of the operating headpiece and to a fluid outlet at a distal end of the elongated insertion tube and to which the fluid supply equipment is connected through the fluid inlet so as to deliver fluid supplied from the fluid supply equipment to the fluid outlet, said fluid delivery adapter unit comprising:

a straight pipe having a first end that is detachably coupled to said fluid inlet;

an elbow pipe having a lock component at a proximal end to which said fluid supply equipment is coupled; and a coupling device for joining said elbow pipe to an opposing second end of said straight pipe so as to allow said elbow pipe to turn with respect to said straight pipe through a predetermined angular range, such that the elbow pipe can be adjusted to a rest position having any angular position with respect to the straight pipe within the predetermined range, said coupling device including a first connection member having a first connection part on said elbow pipe, and a second connection member on said straight pipe having a second connection part that interlocks with said first connection part.

* * * * *